(12) United States Patent
Okuda et al.

(10) Patent No.: US 7,456,971 B2
(45) Date of Patent: Nov. 25, 2008

(54) OPTICAL GAS SENSING APPARATUS

(75) Inventors: Yasuyuki Okuda, Aichi-gun (JP);
Takahiko Yoshida, Okazaki (JP);
Noboru Endo, Anjo (JP)

(73) Assignee: Denso Corporation, Kariya (JP)

( * ) Notice: Subject to any disclaimer, the term of this patent is extended or adjusted under 35 U.S.C. 154(b) by 123 days.

(21) Appl. No.: 11/484,886

(22) Filed: Jul. 12, 2006

(65) Prior Publication Data
US 2007/0012878 A1    Jan. 18, 2007

(30) Foreign Application Priority Data
Jul. 12, 2005  (JP)  ............. 2005-203549

(51) Int. Cl.
*G01N 22/00* (2006.01)
(52) U.S. Cl. ............ 356/437; 356/436; 356/437; 356/443; 250/343; 250/341.8
(58) Field of Classification Search ......... 356/436–443; 250/343, 341.8
See application file for complete search history.

(56) References Cited

U.S. PATENT DOCUMENTS 4,420,687 A * 12/1983 Martinez et al. ............ 356/437

6,201,245 B1 * 3/2001 Schrader ..................... 250/349
6,769,319 B2 * 8/2004 McDonald et al. ............ 73/431
2004/0145260 A1   7/2004 Tamaoka et al.

FOREIGN PATENT DOCUMENTS

JP       A-8-184556       7/1996

\* cited by examiner

*Primary Examiner*—L. G. Lauchman
*Assistant Examiner*—Iyabo S Alli
(74) *Attorney, Agent, or Firm*—Posz Law Group, PLC (57) ABSTRACT

An optical gas sensing apparatus for sensing gas includes a tubular housing member, a column light source member, a column light sensing element member and an adhesive. The tubular housing member has a light-reflecting inner surface. The column light source member is provided to a first end portion of the housing member, wherein the light source member has a light source, which emits light. The column light sensing element member is provided to a second end portion of the housing member, wherein the light sensing element member has a light sensing element, which senses the light emitted by the light source. The adhesive connects the housing member to at least one of the light source member and the light sensing element member.

15 Claims, 5 Drawing Sheets

OPTICAL GAS SENSING APPARATUS

CROSS REFERENCE TO RELATED APPLICATION

This application is based on and incorporates herein by reference Japanese Patent Application No. 2005-203549 filed on Jul. 12, 2005.

BACKGROUND OF THE INVENTION

1. Field of the Invention

The present invention relates to optical gas sensing apparatuses.

2. Description of Related Art

For example, Japanese Unexamined Patent Publication H8-184556 discloses an optical gas sensing apparatus, which includes a light source (light emitting member) and a light sensing element (light receiving member). This optical gas sensing apparatus detects a concentration of measured gas based on an absorbance of light due to the measured gas, which is introduced to a light passage of the light emitted by the light source.

In order to effectively use a light intensity from the light source, a general optical gas sensing apparatus includes a tubular housing member, an inner surface of which reflects the light so that the light is converged to the light sensing element. Also, in order to facilitate assembly and maintenance, the light source and/or the light sensing element are/is mounted on the housing member. Typically, the light source is mounted on a light source member, which caps one end of the housing member. Also, the light sensing element is mounted on a light sensing member, which caps another end of the housing member. Thereby, a closed space is defined by the housing member, the light source member and the light sensing member. The measured gas is introduced to this closed space so that the absorbance of the light, which is absorbed by the measured gas, is sensed by the light sensing element. Thus, the concentration of the measured gas is sensed. Here, the light is emitted by the light source.

In the above structured conventional optical gas sensing apparatus, in order to limit a change of a sensor output, screws are used to fix the housing member and the light source member, and to fix the housing member and the light sensing member instead of press fitting and snap fitting, which may cause erroneous allocation or displacement in some cases. However, the assembly by use of the screw may increase a number of components and a man hour. Thus, a production cost may increase.

SUMMARY OF THE INVENTION

The present invention is made in view of the above disadvantages. Thus, it is an objective of the present invention to address at least one of the above disadvantages.

To achieve the objective of the present invention, there is provided an optical gas sensing apparatus for sensing gas, the optical gas sensing apparatus including a tubular housing member, a column light source member, a column light sensing element member and an adhesive. The tubular housing member has a light-reflecting inner surface. The column light source member is provided to a first end portion of the housing member, wherein the light source member has a light source, which emits light. The column light sensing element member is provided to a second end portion of the housing member, wherein the light sensing element member has a light sensing element, which senses the light emitted by the light source. The adhesive connects the housing member to at least one of the light source member and the light sensing element member.

BRIEF DESCRIPTION OF THE DRAWINGS

The invention, together with additional objectives, features and advantages thereof, will be best understood from the following description, the appended claims and the accompanying drawings in which:

DETAILED DESCRIPTION OF PREFERRED EMBODIMENTS

Best embodiments for carrying out the present invention will be described with reference to accompanying drawings.

Figure 1:
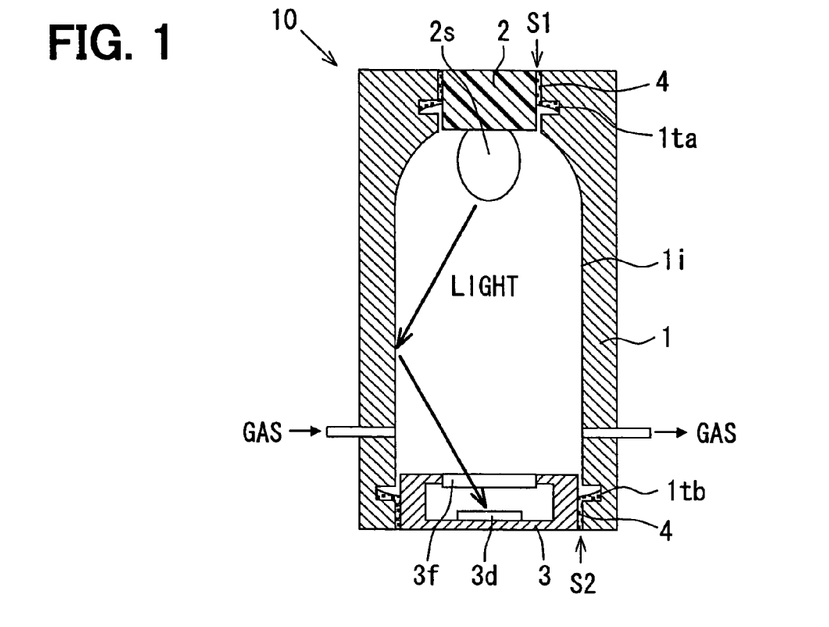
FIG. 1 is a schematic sectional view of an optical gas sensing apparatus according to an example of a present invention.

An optical gas sensing apparatus 10 shown in FIG. 1 includes a tubular housing member 1, a column light source member 2 and a column light sensing element member 3. The housing member 1 has an inner surface (reflecting surface) 11, which reflects light so that the light is converged. The light source member 2 includes a light source 2s and is located on one end portion of the housing member 1. The light sensing element member 3 has a light sensing element 3d and is located on another end portion of the housing member 1. The housing member 1 of the optical gas sensing apparatus 10 is a cylindrical tube, and the light source member 2 and the light sensing element member 3 are cylindrical columns. The light source member 2 and the light sensing element member 3 are both simply received by the cylindrical tube part of the housing member 1. The housing member 1 is connected with the light source member 2 through an adhesive 4, and the housing member 1 is connected with the light sensing element member 3 through the adhesive 4.

The optical gas sensing apparatus 10 has a space defined by the housing member 1, the light source member 2 and the light sensing element member 3. Measured gas (object gas to be measured) is introduce into the space and the light sensing element 3d detects an absorbance of light absorbed by the measured gas. Here, the light is emitted by the light source 2s. Thus, a concentration of the measured gas is detected. Here, a light wavelength selective filter 3f is provided in front of the light sensing element 3d of the light sensing element member 3 so that light of a specific wavelength, which is absorbed by the measured gas, selectively filters through the light wavelength selective filter 3f to be sensed by the light sensing element member 3.

In the optical gas sensing apparatus 10, the housing member 1 and the light source member 2 are joined (connected) and fixed through the adhesive 4. Also, the housing member 1 and the light sensing element member 3 are joined and fixed through the adhesive 4. Therefore, when assembling the housing member 1 and the light source member 2, and when assembling the housing member 1 and the light sensing element member 3, erroneous allocation is limited from occurring compared with a case where press fitting and snap fitting are used for fix in the assembly. Therefore, a sensor characteristic difference, which is caused during the assembly, can be limited because the erroneous allocation of the light source 2s, the reflecting surface 11 and the light sensing element 3d is limited. Also, when compared with conventional screw fix, this adhesive fix limits erroneous displacement caused by vibration even for a long time use. Thus, a reliable sensor characteristic can be maintained. Further, when compared with the screw fix, the adhesive fix does not increase a number of components nor a man hour. Thus, the production cost can be reduced.

In the optical gas sensing apparatus 10 shown in FIG. 1, both the light source member 2, which has the light source 2s, and the light sensing element member 3, which has the light sensing element 3d, are joined and fixed to the housing member 1 through the adhesive 4. However, it is not limited to this. Alternatively, either one of the light source member, which has the light source, and the light sensing element member, which has the light sensing element, may be joined and fixed to the housing member through the adhesive. For example, the housing member may be formed into a shape such that one end of the housing member is closed. In this case, either one of the light source member, which has the light source, and the light sensing element member, which has the light sensing element, may be joined and fixed to an opening end of the housing member though the adhesive to achieve the similar effect.

In the optical gas sensing apparatus 10, recess-shaped collecting members 1ta, 1tb for collecting the adhesive 4 are provided to connections (first and second connections) S1, S2, respectively. Here, the connection S1 is formed between the housing member 1 and the light source member 2. The connection S2 is formed between the housing member 1 and the light sensing element member 3. Specifically, in the optical gas sensing apparatus 10 shown in FIG. 1, the collecting members 1ta, 1tb are provided to surfaces of the housing member 1 (first and second surfaces of the housing member 1) within the connections S1, S2.

In manufacturing the optical gas sensing apparatus 10, the adhesive 4 is applied to the connection S1 located between the housing member 1 and the light source member 2 and the connection S2 located between the housing member 1 and the light sensing element member 3. After assembling the housing member 1, the light source member 2 and the light sensing element member 3, the thermoset adhesive 3 is cured at a high temperature. Because the collecting member 1ta, 1tb are provided to the connections S1, S2, the high-fluidity adhesive 4, which may be highly fluidized by excessive application of the adhesive 4 and heat, can be collected by the collecting members 1ta, 1tb when assembling components and when curing the adhesive 4 at the high temperature. Therefore, the excessive adhesive 4 is limited from overflowing to the reflecting surface 11 of the housing member 1. Thus, the difference of the sensor characteristic, such as a decreased sensitivity caused by a decreased reflectivity due to the overflowed adhesive 4, can be limited.

In the optical gas sensing apparatus 10, the collecting members 1ta, 1tb for collecting the adhesive 4 are provided to both the connections S1, S2, respectively. However, it is not limited to this. Alternatively, only one collecting member may be provided to either one of the connections S1, S2. For example, the collecting member may be provided to a lower-side connection, which is located on a lower side of the housing member 1 during the curing process. In this case, similar effects can be also achieved.

Figure 2A:
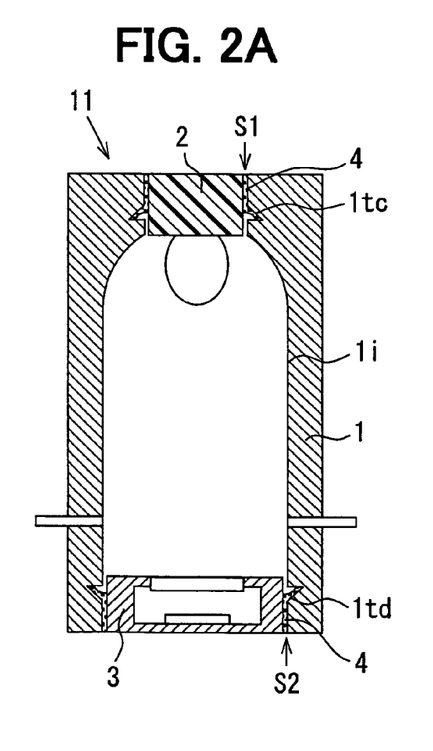
FIG. 2A is a schematic sectional view of an optical gas sensing apparatus according to another example of the present invention.
Figure 2B:
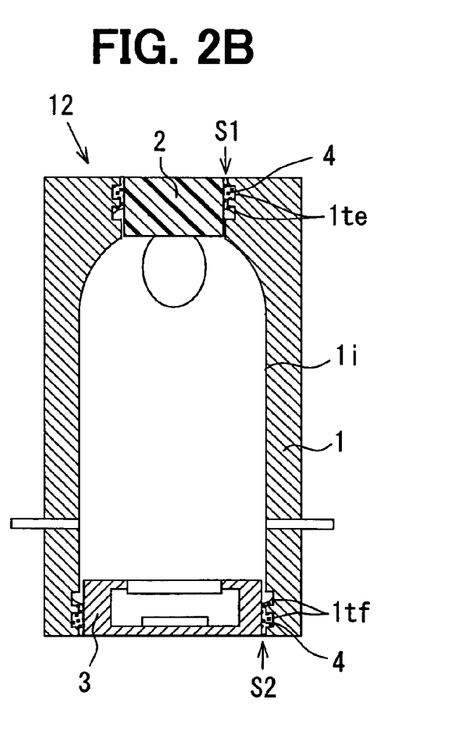
FIG. 2B is a schematic sectional view of an optical gas sensing apparatus according to another example of the present invention.

FIGS. 2A, 2B are schematic sectional views of optical gas sensing apparatuses 11, 12 as other examples of the present invention. In the optical gas sensing apparatuses 11, 12 shown in FIGS. 2A, 2B, similar components similar to the components of the optical gas sensing apparatus 10 shown in FIG. 1 are indicated as the same numerals.

In the optical gas sensing apparatus 11, recess-shaped collecting members 1tc, 1td for collecting the adhesive 4 are provided to the surfaces (first and second surfaces) of the housing member 1 within the connections S1, S2 similarly to the optical gas sensing apparatus 10. In the optical gas sensing apparatus 12, recess-shaped collecting members 1te, 1tf for collecting the adhesive 4 are provided to the surfaces (first and second surfaces) of the housing member 1 within the connections S1, S2 similarly to the optical gas sensing apparatus 10. In contrast, in the optical gas sensing apparatus 11, the cross-sectional shapes of the collecting members 1tc, 1td differ from the cross-sectional shapes of the collecting members 1ta, 1tb of the optical gas sensing apparatus 10. Also, in the optical gas sensing apparatus 12, the collecting members 1te are doubly provided to the connection S1. Also, the collecting members 1tf are doubly provided to the connection S2. As discussed above, the cross-sectional shape of the collecting member can be any shape as long as the collecting member is formed as the recess portion for facilitating the collection of the adhesive. Also, the collecting members can be multiply provided to one surface within a single connection.

Figure 3A:
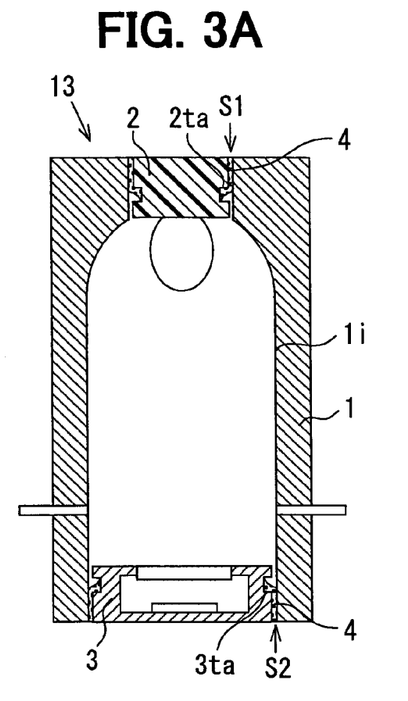
FIG. 3A is a schematic sectional view of an optical gas sensing apparatus according to another example of the present invention.
Figure 3B:
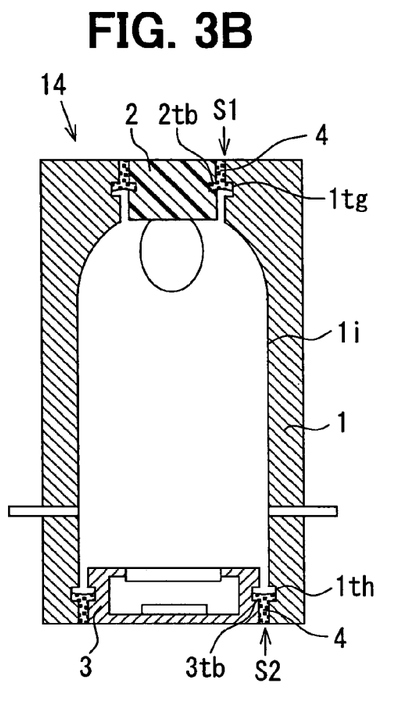
FIG. 3B is a schematic sectional view of an optical gas sensing apparatus according to another example of the present invention.

FIGS. 3A, 3B are schematic sectional views of optical gas sensing apparatuses 13, 14 respectively as other examples of the present invention. In the optical gas sensing apparatuses 13, 14 shown in FIGS. 3A, 3B, similar components similar to the components of the optical gas sensing apparatus 10 shown in FIG. 1 are indicated as the same numerals.

In the optical gas sensing apparatus 10, the collecting members 1ta, 1tb are provided to the surfaces of the housing member 1 within the connections S1, S2. However, in the optical gas sensing apparatus 13 shown in FIG. 3A, collecting member 2ta is provided to a surface of the light source member 2 within the connection S1. Also, collecting member 3ta is provided to a surface of the light sensing element member 3 within the connection S2. In the optical gas sensing apparatus 14 shown in FIG. 3B, collecting members 1tg, 1th are provided to surfaces of the housing member 1 within the connections S1, S2, respectively. Also, collecting members 2tb, 3tb are provided to surfaces of the light source member 2 and the light sensing element member 3 within the connections S1, S2, respectively.

As described above, when the collecting member is provided to at least one of surfaces of the housing member, the light source member and the light sensing element member, the similar effect similar to the case of the optical gas sensing member 10 can be also achieved. When the light source member 2 and the light sensing element member 3 are cylindrical columns and are simply received by (inserted into) the cylindrically tubular housing member 1 as shown in FIGS. 1 to 3B, the surfaces of the light source member 2 and the light sensing element member 3 within the connections S1, S2 respectively correspond to outer peripheral surfaces of the cylindrical columns. Therefore, because the collecting members 2ta, 3ta are provided to the surfaces of the light source member 2 and the light sensing element member 3 within the connections S1, S2 respectively as shown in FIG. 3A, the machining is facilitated and the manufacturing cost of the optical gas sensing apparatus 13 can be reduced.

Figure 4:
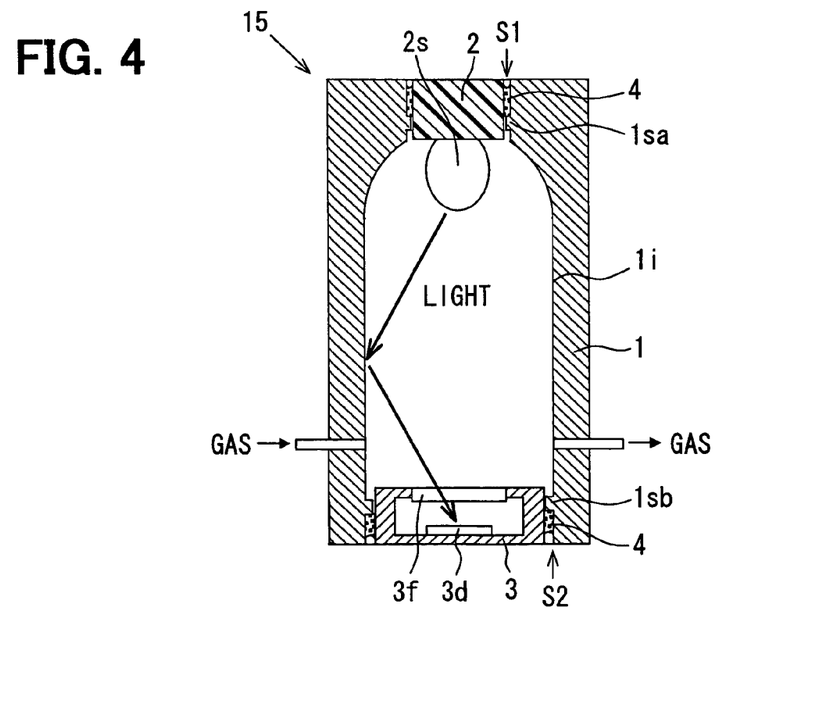
FIG. 4 is a schematic sectional view of an optical gas sensing apparatus according to another example of the present invention.

FIG. 4 is a schematic sectional view of an optical gas sensing apparatus as another example of the present invention. In the optical gas sensing apparatus 15 shown in FIG. 4, similar components similar to the components of the optical gas sensing apparatus 10 shown in FIG. 1 are indicated as the same numerals.

In the optical gas sensing apparatus 10, the recess-shaped collecting members 1ta, 1tb for collecting the adhesive 4 are provided to the connections S1, S2, respectively. The connection S1 is formed between the housing member 1 and the light source member 2. The connection S2 is formed between the housing member 1 and the light sensing element member 3. In contrast, in the optical gas sensing apparatus 15 shown in FIG. 4, protrusion-shaped stopping members 1sa, 1sb for the adhesive 4 are provided to the connections S1, S2 respectively.

In the optical gas sensing apparatus 15, the stopping members 1sa, 1sb limits the adhesive 4, which is excessively applied to the connections S1, S2, during the assembly of the housing member 1, the light source member 2 and the light sensing element member 3. Thus, the excessive adhesive 4 is limited from overflowing to the reflecting surface 1i of the housing member 1. Thus, the difference of the sensor characteristic, such as the decreased sensitivity caused by the decreased reflectivity due to the overflowed adhesive 4, can be limited by the stopping members 1sa, 1sb.

Figure 5A:
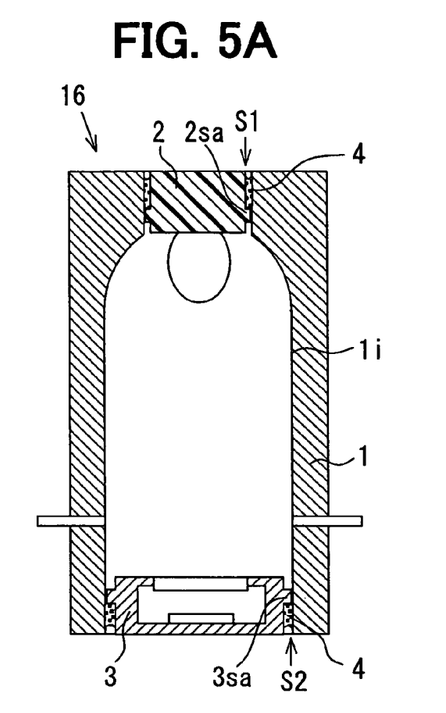
FIG. 5A is a schematic sectional view of an optical gas sensing apparatus according to another example of the present invention.
Figure 5B:
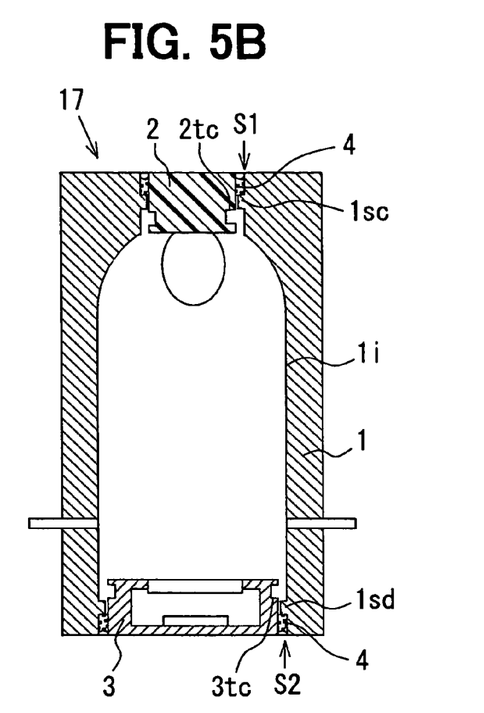
FIG. 5B is a schematic sectional view of an optical gas sensing apparatus according to another example of the present invention.

FIGS. 5A, 5B are schematic sectional views of optical gas sensing apparatuses 16, 17 respectively as other examples of the present invention.

In the optical gas sensing apparatus 15, the stopping members 1sa, 1sb are provided to the surfaces of the housing member 1 within the connections S1, S2. However, in the optical gas sensing apparatus 16 shown in FIG. 5A, a stopping member 2sa is provided to the surface of the light source member 2 within the connection S1. Also, a stopping member 3sa is provided to the surface of the light sensing element member 3 within the connection S2. As described above, the stopping members may be provided to the surfaces of the housing member 1 within the connections S1, S2. Also, alternatively, the stopping members may be provided to the surfaces of the light source member 2 and the light sensing element member 3 within the connections S1, S2, respectively.

Similarly to the optical gas sensing apparatus 13 shown in FIG. 3A, when the light source member 2 and the light sensing element member 3 are cylindrical columns and are simply received by the cylindrically tubular housing member 1, the machining may be facilitated because the stopping members 2sa, 3sa are provided to the surfaces of the light source member 2 and the light sensing element member 3 within the contact surface portions S1, S2, respectively. Thus, the manufacturing cost of the optical gas sensing apparatus 16 can be reduced.

In the optical gas sensing apparatus 17 shown in FIG. 5B, protrusion-shaped stopping members 1sc, 1sd are provided to the surfaces of the housing member 1 within the connections S1, S2, respectively. Recess-shaped collecting members 2tc, 3tc are provided to the surfaces of the light source member 2 and the light sensing element member 3 within the connections S1, S2, respectively. Thus, the stopping members 1sc, 1sd and the collecting members 2tc, 3tc can be combined to collect the highly fluidized adhesive 4, which may be fluidized by the excessive application and heat.

Figure 6:
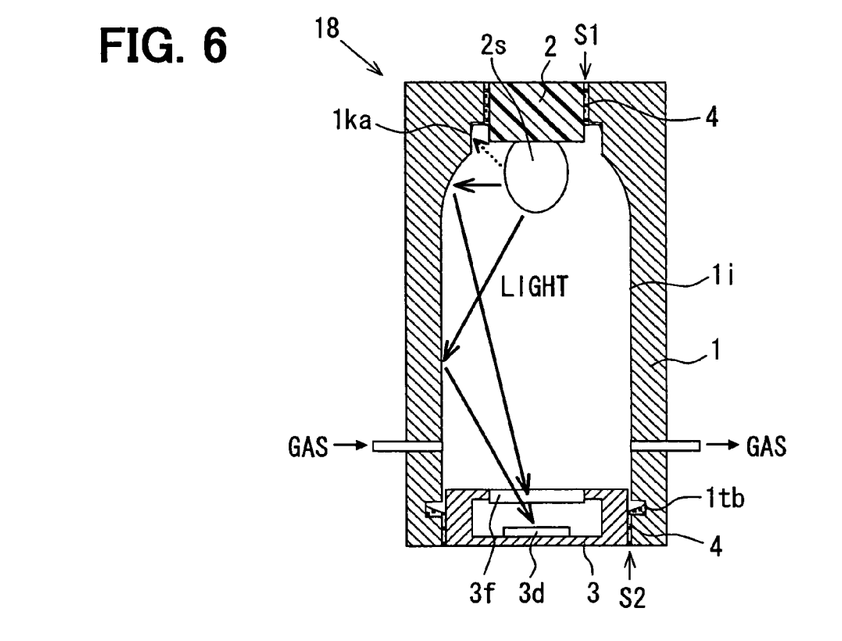
FIG. 6 is a schematic sectional view of an optical gas sensing apparatus according to another example of the present invention.

FIG. 6 is a schematic sectional view of an optical gas sensing apparatus as another example of the present invention. In the optical gas sensing apparatus 18 shown in FIG. 6, similar components similar to the components of the optical gas sensing apparatus 10 shown in FIG. 1 are indicated as the same numerals.

In the optical gas sensing apparatus 10, the recess-shaped collecting members 1ta, 1tb for collecting the adhesive 4 are provided to the connections S1, S2, respectively. The connection S1 is formed between the housing member 1 and the light source member 2. The connection S2 is formed between the housing member 1 and the light sensing element member 3. In contrast, in the optical gas sensing apparatus 18 shown in FIG. 6, recess member 1ka is provided to an inner surface of the housing member 1 at a vicinity of an end portion of the light source member 2. The recess member 1ka does not have a light reflecting passage that allows the light emitted by the light source 2s to reach the light sensing element 3d (i.e., the recess member 1ka is located and formed into a shape such that the light, which travels into the recess member 1ka, will not reach the light sensing element 3d).

Because the recess member 1ka provided to the optical gas sensing apparatus 18 does not have the above light reflecting passage, the recess member 1ka is not related to the sensor characteristic, such as the sensitivity. Thus, even when the excessively applied adhesive 4 to the connection S1 outflows into the recess member 1ka, the designed sensor characteristics, such as the sensitivity, is not changed (influenced). Therefore, the difference of the sensor characteristic, such as the decreased sensitivity, due to the overflowed adhesive 4 that is excessively applied can be limited.

Figure 7:
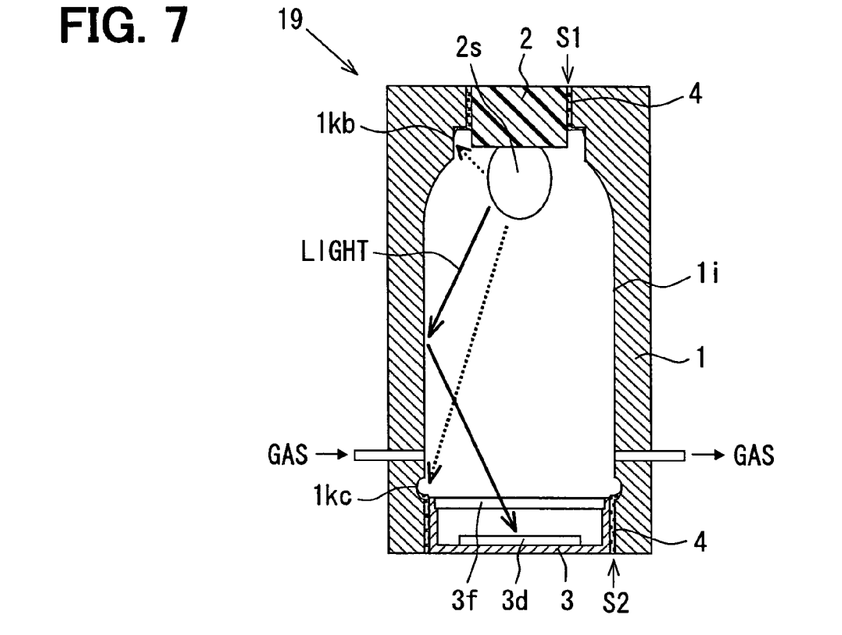
FIG. 7 is a schematic sectional view of an optical gas sensing apparatus according to another example of the present invention.

FIG. 7 is a schematic sectional view of an optical gas sensing apparatus 19 as another example of the present invention.

In the optical gas sensing apparatus 19 shown in FIG. 7, a recess member 1kb is provided to the inner surface of the housing member 1 at the vicinity of the end portion of the light source member 2. Also, a recess member 1kc is provided to an inner surface of the housing member 1 at a vicinity of an end portion of the light sensing element member 3. Each of the recess members 1kb, 1kc does not have the light reflecting passage that allows the light emitted by the light source 2s to reach the light sensing element 3d (i.e., each of the recess members 1kb, 1kc is located and formed into a shape such that the light, which travels into the corresponding one of the recess members 1kb, 1kc, will not reach the light sensing element 3d).

Figure 8:
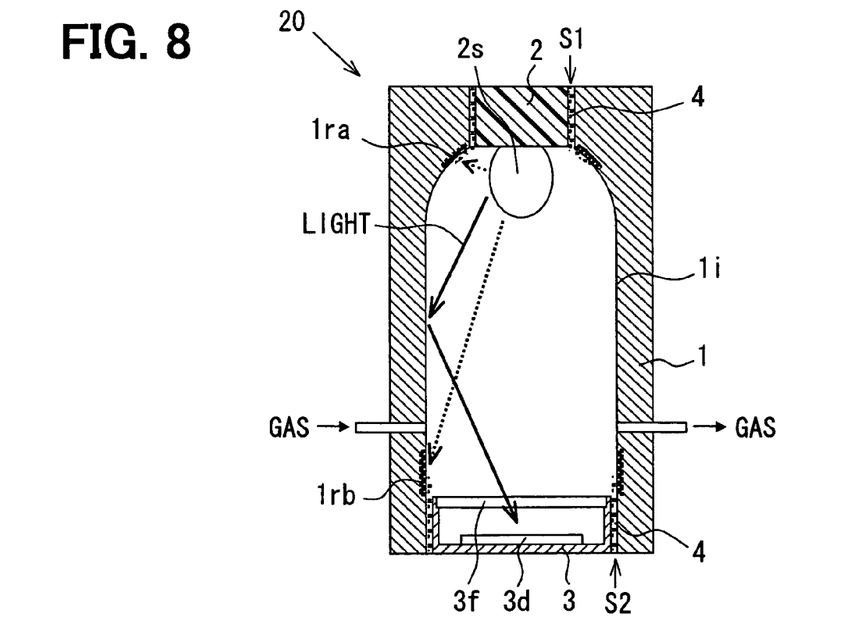
FIG. 8 is a schematic sectional view of an optical gas sensing apparatus according to another example of the present invention.

FIG. 8 is a schematic sectional view of an optical gas sensing apparatus 20 as another example of the present invention. In the optical gas sensing apparatus 20 shown in FIG. 8, similar components similar to the components of the optical gas sensing apparatus 19 shown in FIG. 7 are indicated as the same numerals.

In the optical gas sensing apparatuses 18, 19 shown in FIGS. 6, 7, the recess members 1ka to 1kc are provided to the inner surface of the housing 1 at the vicinities of the light source member 2 and the light sensing element member 3. Each of the recess members 1ka to 1kc does not have the light reflecting passage that allows the light emitted by the light source 2s to reach the light sensing element 3d. In contrast, in the optical gas sensing apparatus 20 shown in FIG. 8, low-reflectivity members 1ra, 1rb are provided to the inner surface of the housing 1 at the vicinities of the light source member 2 and the light sensing element member 3. A light reflectivity of the low-reflectivity members 1ra, 1rb is set lower than the periphery of the low-reflectivity members 1ra, 1rb. The low-reflectivity members 1ra, 1rb may be light absorbing members, which absorb the light, or light scattering members, which scatter the light.

Because the light reflectivity of the low-reflectivity members 1ra, 1rb of the optical gas sensing apparatus 20 is set lower than the periphery, the designed sensor characteristic, such as the sensitivity, is not changed even when the adhesive 4, which is excessively applied to the connections S1, S2, overflows to the low-reflectivity members 1ra, 1rb. Therefore, the difference of the sensor characteristic, such as a decreased sensitivity, due to the overflowed adhesive 4 that is excessively applied can be limited in the case of the optical gas sensing apparatus 20 shown in FIG. 8.

In the above optical gas sensing apparatus, in which the housing member is connected to at least one of the light source member and the light sensing element member through the adhesive, it is preferable to use the adhesive, which absorbs the light of a wavelength. The wavelength here differs from a wavelength, which is absorbed by the measured gas.

Figure 9:
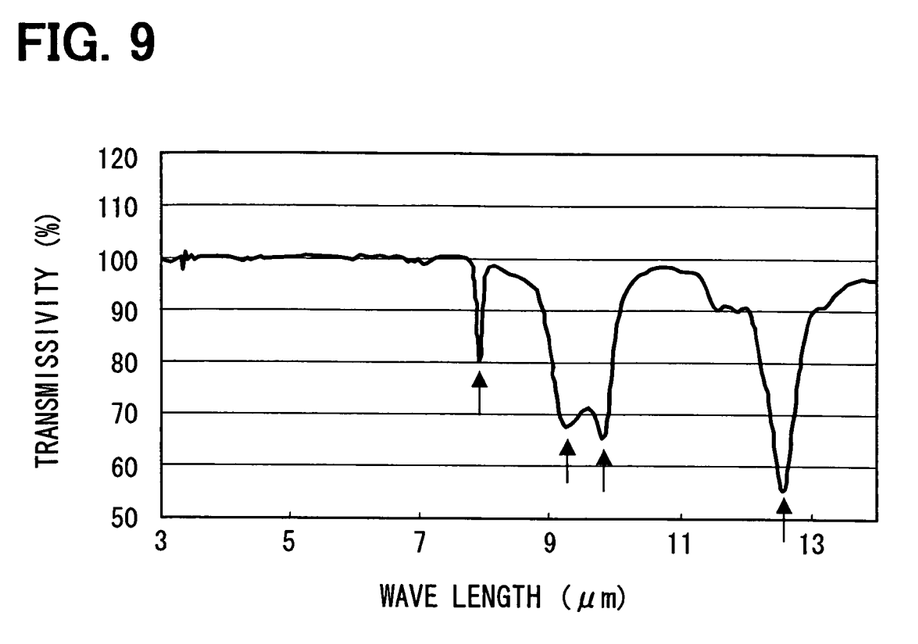
FIG. 9 is a chart of a light transmissibility of an Si adhesive in relation to a light wavelength showing an example of an absorbance range of the light wavelength absorbed by the adhesive.

FIG. 9 is a diagram showing an example of a wavelength of the light that is absorbed by the adhesive. Specifically, it is shown that the light transmissibility of an Si adhesive (TSE322 of Toshiba Silicones) depends on the wavelength of the light. This adhesive absorbs four kinds of light, each of which has one of four wavelengths depicted by arrows in FIG. 9. For example, the optical gas sensing apparatuses 10 to 20 having this adhesive shown in FIGS. 1 to 8 may be used to sense $CO_2$ gas. In this case, the molecules of the $CO_2$ gas absorb the light of the wavelength of 4.26 µm, and this wavelength is different from the wavelength of the light that is absorbed by the adhesive shown in FIG. 9.

Thus, in the above optical gas sensing apparatus, in which the adhesive and the measured gas absorb the different light with different wavelength from each other, a sensing performance for sensing the measured gas may be unaffected even in a case where the adhesive, which is excessively applied to the connection, outflows to the reflecting surface of the housing member. Thus, the difference of the sensing performance for sensing the measured gas due to the overflowed adhesive, which is excessively applied, can be limited by this structure.

As discussed above, the above optical gas sensing apparatus includes the housing member, the light source member and the light sensing element member. Here, the housing member has the inner surface reflecting the light, the light source member has the light source, and the light sensing element member has the light sensing element. The housing member is connected to one of the light source member and the light sensing element member through the adhesive. With this structure, the change of the sensor characteristic due to the erroneous allocation or displacement of the components during the assembly or the long-term use is limited. Thus, the optical gas sensing apparatus can be inexpensively manufactured without increasing the number of the components nor the man hour. It should be noted that in the above described optical gas sensing apparatus, any combination can be applied in selection of the collecting member of the adhesive, the stopping member of the adhesive, one of the recess member and the low-reflective member, and the adhesive, which is determined in consideration of the wavelength of the light absorbed by the measured gas.

Additional advantages and modifications will readily occur to those skilled in the art. The invention in its broader terms is therefore not limited to the specific details, representative apparatus, and illustrative examples shown and described.

What is claimed is:

1. An optical gas sensing apparatus for sensing gas, comprising:
   a tubular housing member that has a light-reflecting inner surface;
   a column light source member that is provided to a first end portion of the housing member, wherein the light source member has a light source, which emits light;
   a column light sensing element member that is provided to a second end portion of the housing member, wherein the light sensing element member has a light sensing element, which senses the light emitted by the light source;
   an adhesive that connects the housing member to at least one of the light source member and the light sensing element member; and
   at least one collecting member, which is provided in at least one of the following positions:
   in a first connection located between the housing member and the light source member; and
   in a second connection located between the housing member and the light sensing element member, wherein
   the at least one collecting member defines a recess,
   the recess includes a space that extends in a direction perpendicular to an axis of the tubular housing member, and
   the adhesive collects in the space.

2. The optical gas sensing apparatus according to claim 1, wherein the light source member and the light sensing element member are inserted into the tubular housing member.

3. The optical gas sensing apparatus according to claim 1, wherein the housing member, the light source member and the light sensing element member are cylindrically shaped.

4. The optical gas sensing apparatus according to claim 1, wherein:
   the first connection includes a first surface of the housing member,
   the first surface of the housing member facing the light source member; the second connection includes a second surface of the housing member, the second surface of the housing member facing the light sensing element member; and
   each of the at least one collecting member is provided to a corresponding one of at least one of the first and second surfaces of the housing member.

5. The optical gas sensing apparatus according to claim 1, wherein:
   the first connection includes a surface of the light source member, the surface of the light source member facing the housing member;

the second connection includes a surface of the light sensing element member, the surface of the light sensing element member facing the housing member; and each of the at least one collecting member is provided to a corresponding one of at least one of the surface of the light source member and the surface of the light sensing element member.

6. The optical gas sensing apparatus according to claim 1, further comprising at least one stopping member, each of which is provided to a corresponding one of at least one of the following positions:

a first connection located between the housing member and the light source member; and a second connection located between the housing member and the light sensing element member, wherein each of the at least one stopping member is formed into a protrusion shape.

7. The optical gas sensing apparatus according to claim 6, wherein:

the first connection includes a first surface of the housing member, the first surface of the housing member facing the light source member;

the second connection includes a second surface of the housing member, the second surface of the housing member facing the light sensing element member; and each of the at least one stopping member is provided to a corresponding one of at least one of the first and second surfaces of the housing member.

8. The optical gas sensing apparatus according to claim 6, wherein:

the first connection includes a surface of the light source member, the surface of the light source member facing the housing member;

the second connection includes a surface of the light sensing element member, the surface of the light sensing element member facing the housing member; and each of the at least one stopping member is provided to a corresponding one of at least one of the surface of the light source member and the surface of the light sensing element member.

9. The optical gas sensing apparatus according to claim 1, further comprising at least one recess member, each of which is located at an inner surface of the housing member at a vicinity of a corresponding one of at least one of an end portion of the light source member and an end portion of the light sensing element member, wherein each of the at least one recess member does not have a light reflecting passage that allows the light emitted by the light source to reach the light sensing element.

10. The optical gas sensing apparatus according to claim 1, further comprising at least one low-reflective member, each of which is located at an inner surface of the housing member at a vicinity of a corresponding one of at least one of an end portion of the light source member and an end portion of the light sensing element member, wherein a reflectivity of each of the at least one low-reflective member is lower than a reflectivity of a periphery.

11. The optical gas sensing apparatus according to claim 10, wherein the at least one low-reflective member includes a light absorbing member that absorbs the light.

12. The optical gas sensing apparatus according to claim 10, wherein the at least one low-reflective member includes a light scattering member that scatters the light.

13. The optical gas sensing apparatus according to claim 1, wherein:

the adhesive absorbs light of a first wavelength;

the gas absorbs light of a second wavelength; and the first wavelength and the second wavelength are different from each other.

14. The optical gas sensing apparatus according to claim 1, wherein:

a space is defined by the tubular housing, the light source member and the light sensing element member;

the gas is introduce to the space; and the light sensing element member senses an absorbance of the light emitted by the light source, the light being absorbed by the gas, so that a concentration of the gas is sensed.

15. The optical gas sensing apparatus according to claim 1, wherein the collecting member defines an annular groove.

* * * * *